(12) United States Patent
Whitfield

(10) Patent No.: US 9,993,229 B2
(45) Date of Patent: Jun. 12, 2018

(54) SPECIMEN RETRIEVAL DEVICE

(71) Applicant: Covidien LP, Mansfield, MA (US)

(72) Inventor: Kenneth H. Whitfield, North Haven, CT (US)

(73) Assignee: COVIDIEN LP, Mansfield, MA (US)

( * ) Notice: Subject to any disclaimer, the term of this patent is extended or adjusted under 35 U.S.C. 154(b) by 953 days.

(21) Appl. No.: 13/664,863

(22) Filed: Oct. 31, 2012

(65) Prior Publication Data

US 2013/0116592 A1 May 9, 2013

Related U.S. Application Data

(60) Provisional application No. 61/557,303, filed on Nov. 8, 2011.

(51) Int. Cl.
  *A61B 10/02* (2006.01)
  *A61B 17/221* (2006.01)
  *A61B 17/00* (2006.01)

(52) U.S. Cl.
  CPC ............ *A61B 10/02* (2013.01); *A61B 17/221* (2013.01); *A61B 2017/00287* (2013.01)

(58) Field of Classification Search
  USPC ........................................ 600/562
  See application file for complete search history.

(56) References Cited

U.S. PATENT DOCUMENTS

| 30,471 A | 10/1860 | Dudley |
|---|---|---|
| 35,164 A | 5/1862 | Logan et al. |
| 156,477 A | 11/1874 | Bradford |
| 1,609,014 A | 11/1926 | Dowd |
| 3,800,781 A | 4/1974 | Zalucki |
| 4,557,255 A | 12/1985 | Goodman |
| 4,611,594 A | 9/1986 | Grayhack et al. |
| 4,744,363 A | 5/1988 | Hasson |
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | Levahn |
| 4,997,435 A | 3/1991 | Demeter |
| 5,037,379 A | 8/1991 | Clayman et al. |

(Continued)

FOREIGN PATENT DOCUMENTS

| DE | 8435489 | 12/1984 |
|---|---|---|
| DE | 3542667 | 6/1986 |

(Continued)

OTHER PUBLICATIONS

Extended European Search Report corresponding to EP No. 12 19 1639.9, completed May 22, 2013, and dated May 31, 20113; (10 pp).

(Continued)

*Primary Examiner* — Jeffrey G Hoekstra
*Assistant Examiner* — Yasmeen S Warsi

(57) ABSTRACT

A suture loop assembly is provided for securing a specimen collection bag in a closed condition. The suture loop assembly generally includes a length of suture material forming a distal loop and a one-way ferrule for securing the distal loop in a closed condition about an upper end of the specimen collection bag. A specimen retrieval device is also provided for use with the suture loop assembly.

15 Claims, 10 Drawing Sheets

(56) References Cited

U.S. PATENT DOCUMENTS

| | | | |
|---|---|---|---|
| 5,074,867 A | 12/1991 | Wilk | |
| 5,084,054 A | 1/1992 | Bencini et al. | |
| 5,143,082 A | 9/1992 | Kindberg et al. | |
| 5,147,371 A | 9/1992 | Washington et al. | |
| 5,176,687 A | 1/1993 | Hasson et al. | |
| 5,190,542 A | 3/1993 | Nakao et al. | |
| 5,190,555 A | 3/1993 | Wetter et al. | |
| 5,190,561 A | 3/1993 | Graber | |
| 5,192,284 A | 3/1993 | Pleatman | |
| 5,192,286 A | 3/1993 | Phan et al. | |
| 5,201,740 A | 4/1993 | Nakao et al. | |
| 5,215,521 A | 6/1993 | Cochran et al. | |
| 5,224,930 A | 7/1993 | Spaeth et al. | |
| 5,234,439 A | 8/1993 | Wilk et al. | |
| 5,279,539 A | 1/1994 | Bohan et al. | |
| 5,312,416 A | 5/1994 | Spaeth et al. | |
| 5,330,483 A | 7/1994 | Heaven et al. | |
| 5,336,227 A | 8/1994 | Nakao et al. | |
| 5,337,754 A | 8/1994 | Heaven et al. | |
| 5,341,815 A * | 8/1994 | Cofone et al. | 600/562 |
| 5,352,184 A | 10/1994 | Goldberg et al. | |
| 5,354,303 A | 10/1994 | Spaeth et al. | |
| 5,368,545 A | 11/1994 | Schaller et al. | |
| 5,368,597 A | 11/1994 | Pagedas | |
| 5,370,647 A | 12/1994 | Graber et al. | |
| 5,465,731 A * | 11/1995 | Bell et al. | 600/562 |
| 5,480,404 A * | 1/1996 | Kammerer et al. | 606/113 |
| 5,486,182 A | 1/1996 | Nakao et al. | |
| 5,486,183 A | 1/1996 | Middleman et al. | |
| 5,499,988 A | 3/1996 | Espiner et al. | |
| 5,524,633 A | 6/1996 | Heaven et al. | |
| 5,535,759 A | 7/1996 | Wilk | |
| 5,611,803 A | 3/1997 | Heaven et al. | |
| 5,618,296 A | 4/1997 | Sorensen et al. | |
| 5,630,822 A | 5/1997 | Hermann et al. | |
| 5,643,282 A | 7/1997 | Kieturakis | |
| 5,643,283 A | 7/1997 | Younker | |
| 5,645,083 A | 7/1997 | Essig et al. | |
| 5,647,372 A | 7/1997 | Tovey et al. | |
| 5,649,902 A | 7/1997 | Yoon | |
| 5,658,296 A | 8/1997 | Bates et al. | |
| 5,679,423 A | 10/1997 | Shah | |
| 5,735,289 A | 4/1998 | Pfeffer et al. | |
| 5,755,724 A | 5/1998 | Yoon | |
| 5,759,187 A | 6/1998 | Nakao et al. | |
| 5,769,794 A | 6/1998 | Conlan et al. | |
| 5,785,677 A | 7/1998 | Auweiler | |
| 5,788,709 A | 8/1998 | Riek et al. | |
| 5,792,145 A | 8/1998 | Bates et al. | |
| 5,814,044 A | 9/1998 | Hooven | |
| 5,829,440 A | 11/1998 | Broad, Jr. | |
| 5,836,953 A | 11/1998 | Yoon | |
| 5,853,374 A | 12/1998 | Hart et al. | |
| 5,895,392 A | 4/1999 | Riek et al. | |
| 5,906,621 A | 5/1999 | Secrest et al. | |
| 5,957,884 A | 9/1999 | Hooven | |
| 5,971,995 A | 10/1999 | Rousseau | |
| 5,980,544 A | 11/1999 | Vaitekunas | |
| 5,997,547 A | 12/1999 | Nakao et al. | |
| 6,004,330 A | 12/1999 | Middleman et al. | |
| 6,007,512 A | 12/1999 | Hooven | |
| 6,019,770 A | 2/2000 | Christoudias | |
| 6,036,681 A | 3/2000 | Hooven | |
| 6,059,793 A | 5/2000 | Pagedas | |
| 6,123,701 A | 9/2000 | Nezhat | |
| 6,152,932 A | 11/2000 | Temström | |
| 6,162,235 A | 12/2000 | Vaitekunas | |
| 6,165,121 A | 12/2000 | Alfemess | |
| 6,168,603 B1 | 1/2001 | Leslie et al. | |
| 6,228,095 B1 | 5/2001 | Dennis | |
| 6,270,505 B1 | 8/2001 | Yoshida et al. | |
| 6,277,083 B1 | 8/2001 | Eggers et al. | |
| 6,280,450 B1 | 8/2001 | McGuckin, Jr. | |
| 6,344,026 B1 | 2/2002 | Burbank et al. | |
| 6,348,056 B1 | 2/2002 | Bates et al. | |
| 6,350,266 B1 | 2/2002 | White et al. | |
| 6,350,267 B1 | 2/2002 | Stefanchik | |
| 6,383,195 B1 | 5/2002 | Richard | |
| 6,383,196 B1 | 5/2002 | Leslie et al. | |
| 6,383,197 B1 | 5/2002 | Conlon et al. | |
| 6,406,440 B1 | 6/2002 | Stefanchik | |
| 6,409,733 B1 | 6/2002 | Conlon et al. | |
| 6,419,639 B2 | 7/2002 | Walther et al. | |
| 6,447,523 B1 | 9/2002 | Middleman et al. | |
| 6,471,659 B2 | 10/2002 | Eggers et al. | |
| 6,506,166 B1 | 1/2003 | Hendler et al. | |
| 6,508,773 B2 | 1/2003 | Burbank et al. | |
| 6,537,273 B1 | 3/2003 | Sosiak et al. | |
| 6,589,252 B2 | 7/2003 | McGuckin, Jr. | |
| 6,752,811 B2 | 6/2004 | Chu et al. | |
| 6,755,779 B2 | 6/2004 | Vanden Hoek et al. | |
| 6,780,193 B2 | 8/2004 | Leslie et al. | |
| 6,805,699 B2 | 10/2004 | Shimm | |
| 6,840,948 B2 | 1/2005 | Albrecht et al. | |
| 6,872,211 B2 | 3/2005 | White et al. | |
| 6,887,255 B2 | 5/2005 | Shimm | |
| 6,994,696 B2 | 2/2006 | Suga | |
| 7,052,454 B2 | 5/2006 | Taylor | |
| 7,052,501 B2 | 5/2006 | McGuckin, Jr. | |
| 7,090,637 B2 | 8/2006 | Danitz et al. | |
| 7,270,663 B2 | 9/2007 | Nakao | |
| 7,273,488 B2 | 9/2007 | Nakamura et al. | |
| 7,410,491 B2 | 8/2008 | Hopkins et al. | |
| 7,547,310 B2 | 6/2009 | Whitfield | |
| 7,670,346 B2 | 3/2010 | Whitfield | |
| 7,819,121 B2 | 10/2010 | Amer | |
| 8,057,485 B2 | 11/2011 | Hollis et al. | |
| 2002/0068943 A1 | 6/2002 | Chu et al. | |
| 2002/0082516 A1 | 6/2002 | Stefanchik | |
| 2003/0073970 A1 | 4/2003 | Suga | |
| 2003/0100919 A1 | 5/2003 | Hopkins et al. | |
| 2003/0199915 A1 | 10/2003 | Shimm | |
| 2003/0216773 A1 | 11/2003 | Shimm | |
| 2004/0097960 A1 | 5/2004 | Terachi et al. | |
| 2004/0138587 A1 | 7/2004 | Lyons | |
| 2005/0085808 A1 | 4/2005 | Nakao | |
| 2005/0165411 A1 | 7/2005 | Orban, III | |
| 2005/0267492 A1 | 12/2005 | Poncet et al. | |
| 2006/0030750 A1 | 2/2006 | Amer | |
| 2006/0052799 A1 | 3/2006 | Middleman et al. | |
| 2006/0058776 A1 | 3/2006 | Bilsbury | |
| 2006/0058844 A1 * | 3/2006 | White | A61B 17/0057 606/232 |
| 2006/0169287 A1 | 8/2006 | Harrison et al. | |
| 2006/0200169 A1 | 9/2006 | Sniffin | |
| 2006/0200170 A1 | 9/2006 | Aranyi | |
| 2006/0229639 A1 | 10/2006 | Whitfield | |
| 2006/0229640 A1 | 10/2006 | Whitfield | |
| 2007/0016224 A1 | 1/2007 | Nakao | |
| 2007/0016225 A1 | 1/2007 | Nakao | |
| 2007/0073251 A1 | 3/2007 | Zhou et al. | |
| 2007/0088370 A1 | 4/2007 | Kahle et al. | |
| 2007/0135780 A1 | 6/2007 | Pagedas | |
| 2007/0135781 A1 | 6/2007 | Hart | |
| 2007/0186935 A1 | 8/2007 | Wang et al. | |
| 2008/0188766 A1 | 8/2008 | Gertner | |
| 2008/0221588 A1 | 9/2008 | Hollis et al. | |
| 2008/0234696 A1 | 9/2008 | Taylor et al. | |
| 2008/0243145 A1 * | 10/2008 | Whitfield et al. | 606/143 |
| 2008/0300621 A1 | 12/2008 | Hopkins et al. | |
| 2008/0312496 A1 | 12/2008 | Zwolinski | |
| 2009/0082779 A1 | 3/2009 | Nakao | |
| 2009/0138042 A1 * | 5/2009 | Thal | A61B 17/0401 606/232 |
| 2009/0182292 A1 | 7/2009 | Egle et al. | |
| 2009/0192510 A1 | 7/2009 | Bahney | |
| 2009/0209946 A1 * | 8/2009 | Swayze et al. | 606/1 |
| 2009/0240238 A1 | 9/2009 | Grodrian et al. | |
| 2010/0000471 A1 | 1/2010 | Hibbard | |
| 2010/0292732 A1 * | 11/2010 | Hirotsuka | A61B 17/0401 606/232 |
| 2011/0184434 A1 | 7/2011 | Parihar et al. | |
| 2011/0190781 A1 | 8/2011 | Collier et al. | |

(56) References Cited

U.S. PATENT DOCUMENTS

| | | |
|---|---|---|
| 2011/0299799 A1 | 12/2011 | Towe |
| 2012/0046667 A1 | 2/2012 | Cherry |
| 2013/0023895 A1 | 1/2013 | Saleh |

FOREIGN PATENT DOCUMENTS

| | | |
|---|---|---|
| DE | 4204210 | 8/1992 |
| DE | 19624826 | 1/1998 |
| EP | 0947166 | 10/1999 |
| EP | 1685802 | 8/2006 |
| EP | 2 005 900 A2 | 12/2008 |
| EP | 2 184 014 | 5/2010 |
| FR | 1272412 | 9/1961 |
| GB | 2460099 | 11/2009 |
| WO | WO 93/15675 | 8/1993 |
| WO | WO 95/09666 | 4/1995 |
| WO | WO 01/35831 | 5/2001 |
| WO | WO 2004/002334 A1 | 1/2004 |
| WO | WO 2004/112571 | 12/2004 |
| WO | WO 2005/0112783 A1 | 12/2005 |
| WO | WO 2006/110733 | 10/2006 |
| WO | WO 2008/114234 | 9/2008 |

OTHER PUBLICATIONS

Extended European Search Report corresponding to EP No. 13 17 0118.7. completed Nov. 25, 2013 and dated Dec. 5, 2013; (10 pp).
International Search Report corresponding to European Application No. EP 12 16 5852 completed Jun. 13, 2012 and dated Jun. 20, 2012.
http://www.biomaterials.org/week/bio17.cfm, definition and examples of hydrogels.
Partial International Search Report corresponding to EP 12191639.9, dated Feb. 20, 2013; 6 pp.
Extended European Search Report corresponding to EP No. 11 25 0837.9, completed Sep. 3, 2013 and dated Sep. 10, 2013; (7 pp).
Extended European Search Report corresponding to EP No. 11 25 0838.7, completed Sep. 3, 2013 and dated Sep. 10, 2013; (5 pp).

* cited by examiner

SPECIMEN RETRIEVAL DEVICE

CROSS REFERENCE TO RELATED APPLICATION

The present application claims the benefit of and priority to U.S. Provisional Application Ser. No. 61/557,303, filed on Nov. 8, 2011, the entire contents of which are incorporated herein by reference.

BACKGROUND

1. Technical Field

The present disclosure relates to a specimen retrieval device, and more particularly, to a specimen retrieval device for use in surgical procedures.

2. Background of Related Art

In minimally invasive surgical procedures, operations are carried out within the body by using elongated instruments inserted through small entrance openings in the body. The initial opening in the body tissue to allow passage of instruments to the interior of the body may be a natural passageway of the body, or it can be created by a tissue piercing instrument such as a trocar, or created by a small incision into which a cannula is inserted.

Because the tubes, instrumentation, and any required punctures or incisions are relatively small, the surgery is less invasive as compared to conventional surgical procedures in which the surgeon is required to cut open large areas of body tissue. Therefore, minimally invasive surgery minimizes trauma to the patient and reduces patient recovery time and hospital costs.

Minimally invasive procedures may be used for partial or total removal of body tissue or organs from the interior of the body, e.g. nephrectomy, cholecystectomy, lobectomy and other procedures including thoracic, laparoscopic and endoscopic procedures. During such procedures, it is common that a cyst, tumor, or other affected tissue or organ needs to be removed via the access opening in the skin, or through a cannula. Various types of entrapment devices have been disclosed to facilitate this procedure. In many procedures where cancerous tumors are removed, removal of the specimen in an enclosed environment is highly desirable to prevent seeding of cancer cells.

In minimally invasive thoracic surgery, access to the thoracic cavity is limited as well as maneuverability within the cavity as the access port is placed between the confined space between a patient's ribs. Such procedures, commonly referred to as video assisted thoracoscopic surgery (VATS), aim to reduce patient recovery time by accessing the thoracic cavity through the natural intercostal space without spreading the ribs as in open procedures. This restricted access can sometimes cause problems when removing large specimens. Moreover, in such procedures, e.g. thorascopic wedge resection and lobectomy, it is often necessary to remove a portion of the lung and retrieve it relatively intact for pathology. It is also important that the specimen be sufficiently contained to prevent seeding of cancer cells during manipulation and removal.

Therefore, a need exists for a specimen retrieval or removable device having a system for closing and maintaining a collection bag in a closed condition after receiving a tissue sample. There further exists a need for specimen retrieval or removal device incorporating and actuating mechanism capable of remotely closing a collection bag.

SUMMARY

There is disclosed in one aspect a specimen retrieval device comprising a suture loop assembly including a length of suture material having a double strand central portion and a single-strand distal loop portion extending distally from the central portion. The suture loop assembly additionally includes a one-way ferrule defining a bore such that the double strand central portion passes through the bore of the one-way ferrule. The suture material is engageable with a specimen retrieval bag.

The length of suture material can include a pull loop extending proximally from the double strand central portion.

The suture loop assembly may further include an elongate tubular member defining a bore and having a distal portion, wherein the one-way ferrule is positioned within the distal portion and the double strand central portion extends through the bore.

The length of suture material can be a single continuous length of suture material. In one embodiment, the continuous length of suture material is formed by molding a source material. In an alternative embodiment, the continuous length of suture material is formed by securing free ends of a source material together.

In one embodiment, the continuous length of suture material is formed of a synthetic material while in an alternative embodiment, the continuous length of suture material is formed of a natural material.

There is also disclosed in another aspect a specimen retrieval device including a handle portion having a take-up spool, an elongate tubular member extending distally from the handle portion and a collection bag extending from a distal end of the elongate tubular member. A suture loop assembly is engageable with the collection bag and extends proximally through the elongate tubular member. The suture loop assembly includes a length of suture having a distal loop engageable with the collection bag, a central portion and a proximal end. The suture loop assembly further includes a one-way ferrule positioned within the elongate tubular member and about the central portion.

In some embodiments, the take-up spool is engageable with the proximal end of the length of suture and a trigger is engageable with the take-up spool to rotate the take-up spool and close the collection bag. The handle portion can further include a longitudinal movable rack engageable with the trigger and the take-up spool. The handle portion can additionally include a take-up gear provided on the take-up spool and a transmission gear engageable with the take-up gear including a drive gear engageable with the longitudinally movable rack. A return spring can be provided engageable with the trigger to maintain the trigger in a pre-fired condition.

There is still further disclosed in another aspect a method of retrieving a tissue specimen from within a body cavity. The method includes providing a specimen retrieval device having an elongate tubular member, a collection bag extending from a distal end of the elongate tubular member and a suture loop assembly including a length of suture material having a central portion and a distal loop portion passing through an open upper end of the collection bag. A one-way ferrule is positioned within the distal end of the elongate tubular member and the central portion of the length of suture material passes through the one-way ferrule.

The method further includes the steps of placing a tissue specimen through the open upper end of the collection bag, retracting a central portion of the length of suture material to close the distal loop portion of the length of suture material about the open upper end of the collection bag to create a closed upper end of the collection bag, wherein the central portion of the length of suture material is secured within the one-way ferrule in the retracted position.

In one embodiment of the method, the central portion of the length of suture material is secured within the one-way ferrule by engagement of the central portion of the length of suture material with inwardly projecting fingers formed in one-way ferrule.

In one embodiment, the central portion of the length of suture material is severed between the collection bag and the one-way ferrule. In another embodiment, the central portion of the length of the suture material is severed proximally of the one-way ferrule.

In some embodiments, the step of retracting the central portion winds the suture about a take-up spool in the apparatus.

DESCRIPTION OF THE DRAWINGS

An embodiment of the presently disclosed specimen retrieval device is disclosed herein with reference to the drawings, wherein.

DETAILED DESCRIPTION OF EMBODIMENTS

An embodiment of the presently disclosed specimen retrieval device will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
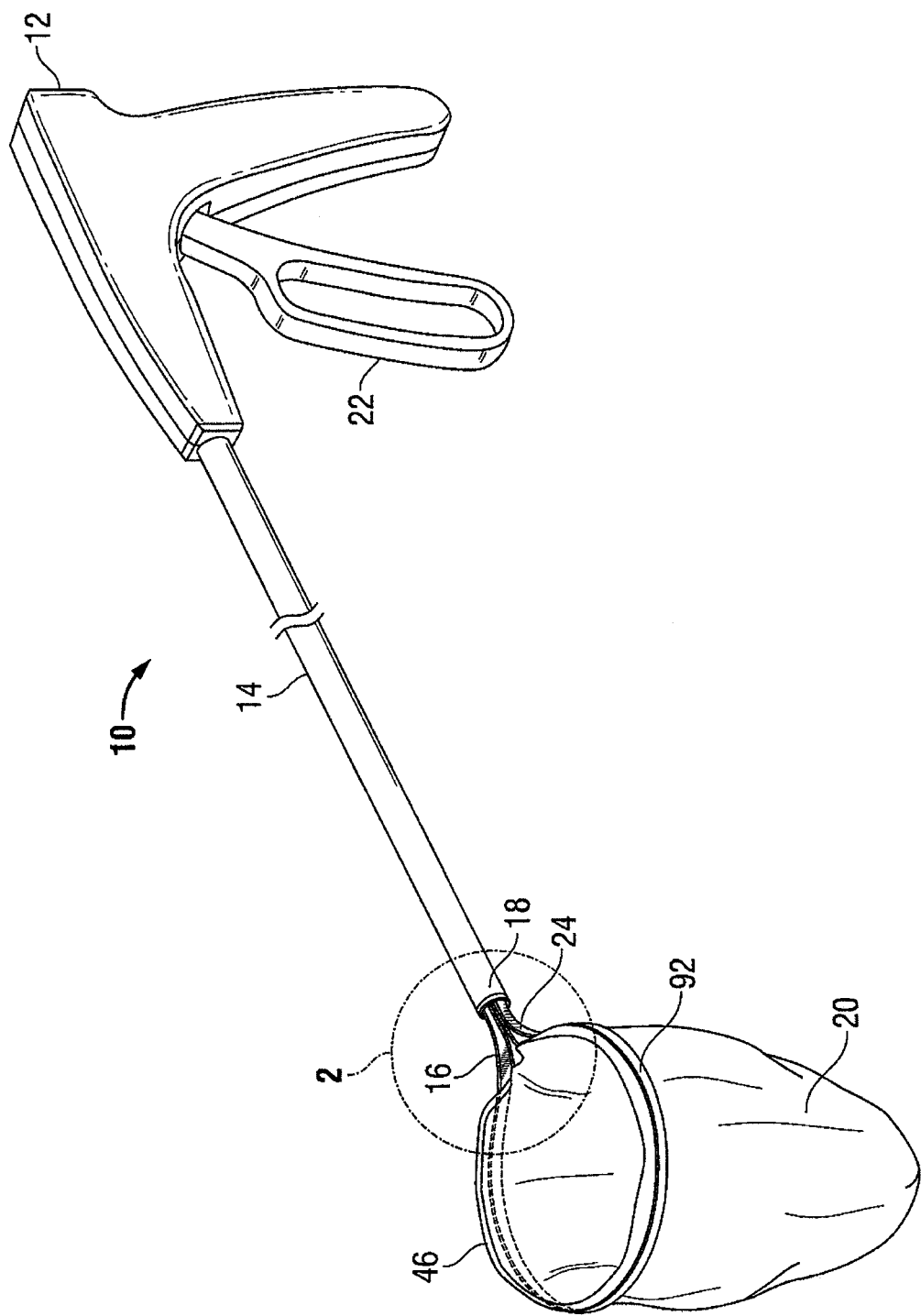
FIG. 1 is a perspective view of the presently disclosed specimen retrieval device.
Figure 2:
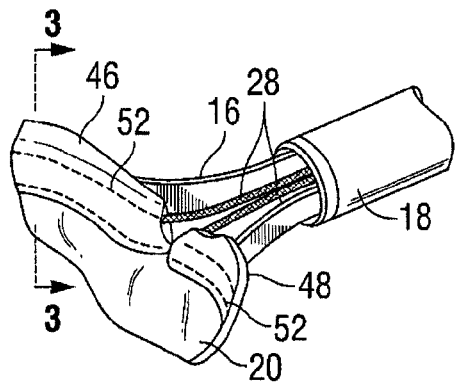
FIG. 2 is an enlarged perspective view of a distal end portion of the specimen retrieval device of FIG. 1.
Figure 3:
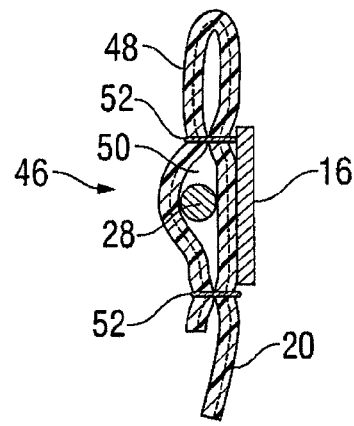
FIG. 3 is a cross sectional view taken along line 3-3 of FIG. 2.

Referring to FIGS. 1-3, and initially to FIG. 1, there is disclosed an embodiment of specimen retrieval device 10 for use in removing organs or other tissues during a surgical procedure. The retrieval device 10 can be used in minimally invasive procedures such as laparoscopic and thoracic procedures.

Specimen retrieval device 10 generally includes body or handle portion 12 and an elongate tubular member 14 extending distally from handle portion 12. A flexible support frame or band 16 extends from a distal end 18 of elongate tubular member 14. In order to catch and remove tissue from the body of a patient, specimen retrieval device 10 includes a collection bag 20 which is releasably supported on and held open by flexible support band 16 as described in more detail hereinbelow. A trigger 22 is movably mounted on handle portion 12 and is provided to actuate specimen retrieval device 10 and close collection bag 20.

Figure 1A:
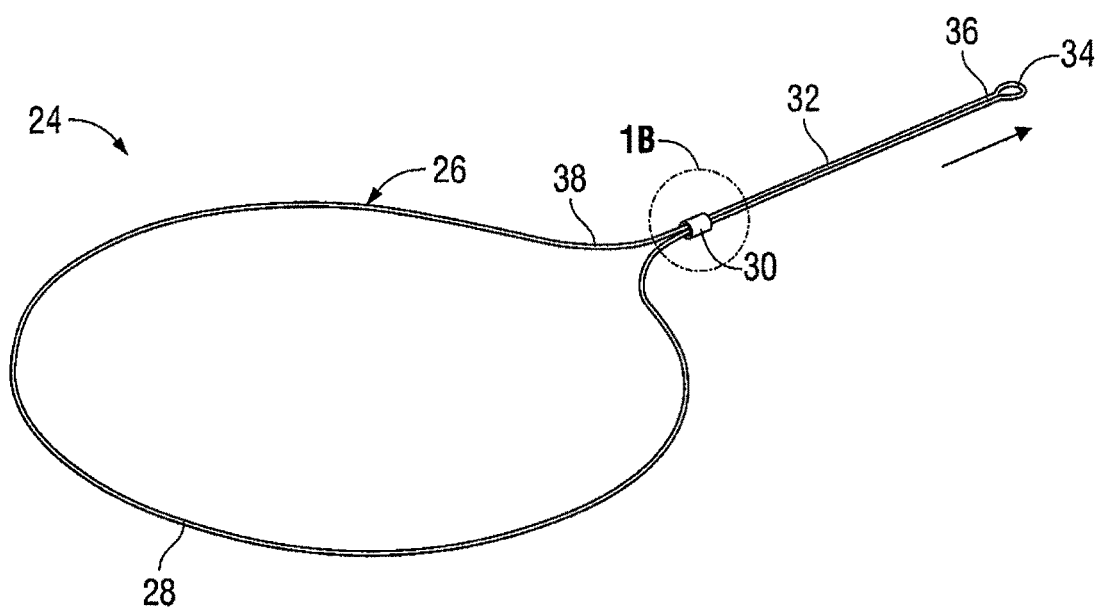
FIG. 1a is a perspective view of a suture loop and one-way ferrule of the specimen retrieval device.
Figure 1B:
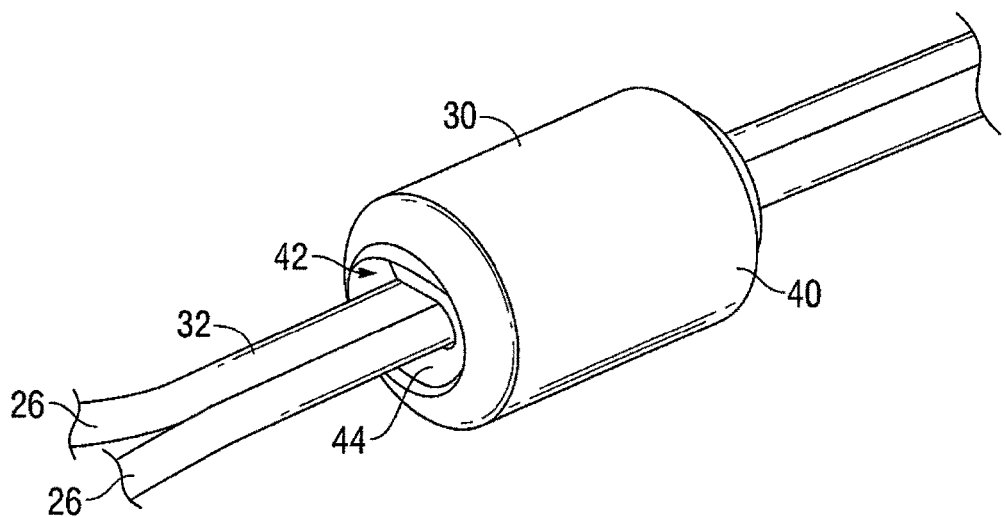
FIG. 1b is an enlarged perspective view of a central portion of the suture loop of FIG. 1a passing through the one-way ferrule.

Referring to FIGS. 1, 1a and 1b, in order to close collection bag 20 about a captured tissue, a suture loop assembly 24 is provided to close and secure collection bag 20. Suture loop assembly 24 extends proximally through elongate tubular member 14 and into handle portion 12. With specific reference to FIG. 1a, suture loop assembly 24 includes a continuous length of suture material 26 having a distal loop portion 28 which engages collection bag 20, e.g. fits within a circumferential pocket adjacent the mouth of the bag described below. Suture loop assembly 24 further includes a one-way ferrule 30 which surrounds a central portion 32 of continuous length of suture material 26 and is provided to secure collection bag 20 in a closed condition once a tissue specimen has been received in collection bag 20. Finally, a pull loop 34 is provided at a proximal end 36 of cental portion 32. Pull loop 34 is positioned within handle portion 12 and is engaged by actuation of trigger 22 to draw distal loop portion 28, formed at a distal end 38 of central portion 32, closed about collection bag 20 and pull central portion 32 through one-way ferrule 30 to secure collection bag 20 in the closed condition. Alternatively, suture loop assembly 24 may be utilized independently and in conjunction with a straight tube (not shown) in which instance pull loop 34 is grasped by the hand of the user and pulled to close and secure collection bag 20.

As noted hereinabove, distal loop portion 28, central portion 32 and pull loop 34 are formed from continuous length of suture material 26. The continuous length configuration of suture material 26 may be formed by molding the material forming suture material 26 as a continuous unit or, alternatively, providing a length of suture material which is then glued, welded, or otherwise affixed back upon itself to form the continuous length of suture material 26. Suture material 26 can be formed from a variety of synthetic or natural, solid or braid materials, such as, for example, polymers, nylons, cottons, flexible metallics, etc.

Continuous length of suture material 26 forms a double strand of suture material 26 as it passes through one-way ferrule 30. This provides an advantage as continuous length of suture material 26 is utilized to close collection bag 20 (FIG. 1). In contrast to pulling on a single length or strand of suture, by pulling on pull loop 34 to draw double strand of central portion 32 through one-way ferrule 30, the length of pull or stroke required to close collection bag 20 due to the double strand is reduced, i.e., cut in half. Additionally, by doubling the strands of continuous length of suture material 26, a reduction in the force required close collection bag 20 is achieved. The doubling of the strands of continuous length of suture material 26 additionally reduces the friction as it is drawn through collection bag 20.

With specific reference to FIG. 1b, one-way ferrule 30 is an elongate cylindrical member 40 having a through bore 42 for receipt of central portion 32 of continuous length of suture material 26. One-way ferrule 30 includes a securing member 44 which projects inwardly into bore 42 in order to frictionally secure central portion 32 as it is drawn through one-way ferrule 30.

Referring now to FIGS. 1, 2 and 3, as noted above, collection bag 20 is releasably supported and held open by flexible support band 16. Collection bag 20 may be temporarily attached to flexible support band 16 by various known methods, such as, for example, tack welding, glueing, etc. Distal loop portion 28 of suture loop assembly 24 is provided to close collection bag 20 after receipt of tissue. Distal loop portion 28 extends around an upper open end 46 of collection bag 20. As best shown in FIGS. 2 and 3, upper open end 46 is folded over to form a folded section 48 defining a channel or pocket 50 for passage of distal loop portion 28. Folded section 48 may be formed by glueing, welding or otherwise fastening upper open end 46 back upon itself. For example, fasteners, such as small staples 52, may be use to hold upper open end 46 into folded section 48.

Figure 4:
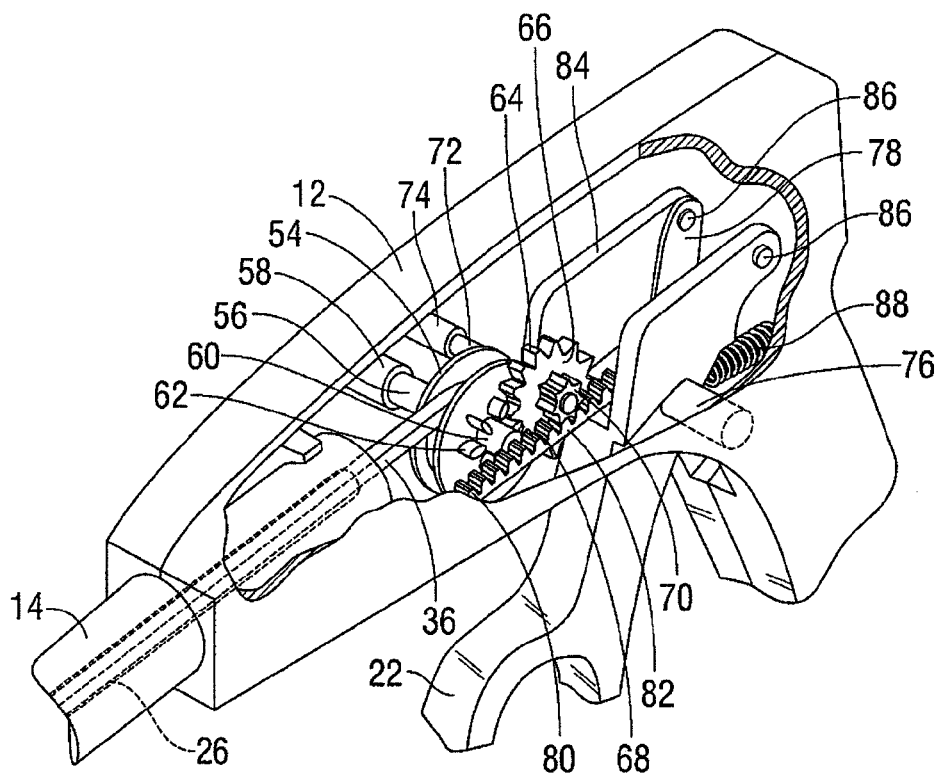
FIG. 4 is a perspective view, partially shown in section, of a handle portion of the specimen retrieval device.

Referring now to FIG. 4, handle portion 12 is provided to draw or take up continuous length of suture material 26 in order to close open upper end 46 of collection bag 20. Specifically, proximal end 36 of continuous length of suture material 26 is wound around a take up spool 54 which is rotatably mounted on a shaft 56 affixed in a mount 58 formed in handle portion 12. Take up spool 54 includes a take up gear 60 having a plurality of teeth 62. Teeth 62 of take up gear 60 are engaged with teeth 64 of a transmission gear 66. Transmission gear 66 includes a drive gear 68 having drive teeth 70. Transmission gear 66 and drive gear 68 are affixed together and are rotatably mounted on a shaft 72 affixed to a mount 74 formed in handle portion 12.

As noted hereinabove, trigger 22 is movably mounted to handle portion 12. Trigger 22 is pivotably mounted about a trigger pivot pin 76 affixed within handle portion 12. In order to rotate take up spool 54, and thus pull continuous length of suture material 26 to close collection bag 20, linkages 78 are provided and connect trigger 22 to a drive rack 80 having drive piece 82 which rotates drive gear 68. Linkages 78 are connected to upwardly extending ears 84 of trigger 22 by pins 86. Additionally, a return spring 88 is provided between trigger 22 and body portion 12 to maintain trigger 22 in a pre-fired condition. Specifically, drive rack teeth 82 engage and rotate drive teeth 70 on drive gear 68 as drive rack 80 is translated longitudinally within handle portion 12 is a response to actuation of trigger 22.

Figure 5:
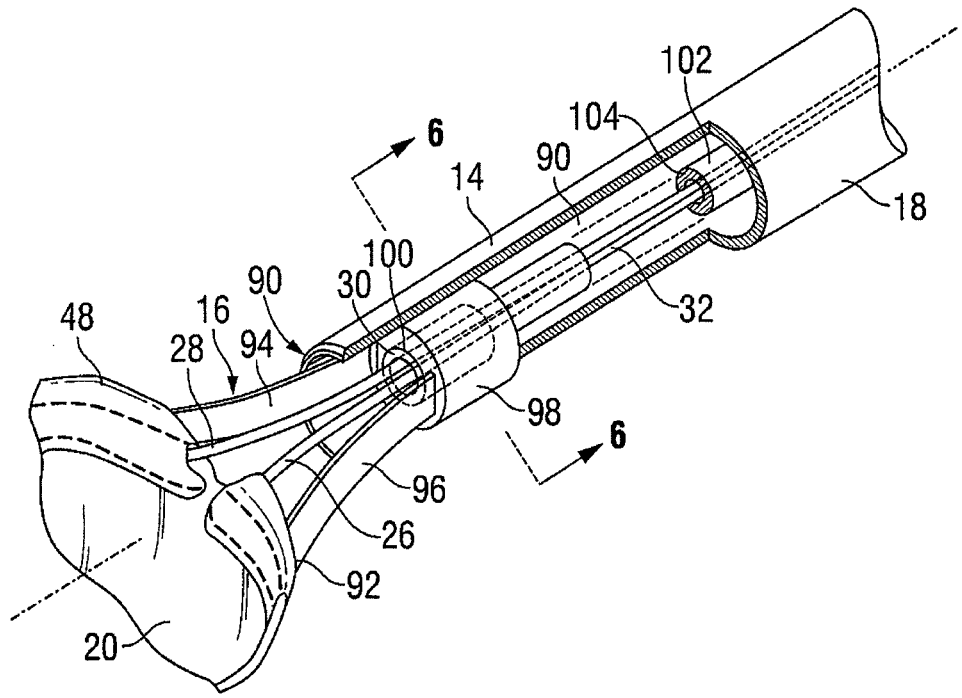
FIG. 5 is a perspective view, partially shown in section, of a distal end portion of the specimen retrieval device.

Referring now to FIG. 5, elongate tubular member 14 defines a bore 90 for receipt of one-way ferrule 30. As noted herein above, flexible support band 16 is provided to support collection bag 20. Flexible support band 16 includes a distally extending loop 92 releasably affixed to collection bag 20 and first and second proximal ends 94 and 96 which are received within bore 90 in elongate tubular member 14. Specifically, a support collar 98 is provided within bore 90 and secures first and second proximal ends 94 and 96 of flexible support band 16 within the elongate tubular member 14. In this embodiment, one-way ferrule 30 is located within a bore 100 of support collar 98. One-way ferrule 30 may be affixed within bore 100 of support collar 98 or as described in more detail him below, may be releasably supported within bore 100 of support collar 90. An elongate tubular or suture guide 102 having a through bore 104 extends from one-way ferrule 30 proximally through bore 90 of elongate tubular member 14 to support proximal portion 32 of suture material 26 within through bore 104.

Figure 6:
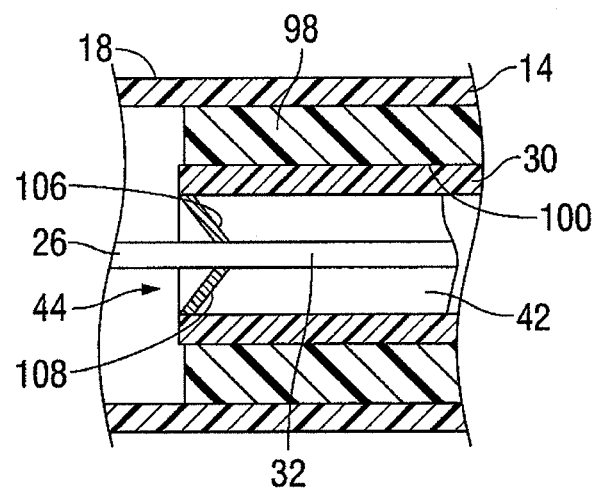
FIG. 6 is a cross sectional view taken along line 6-6 of FIG. 5.

Referring to FIG. 6, one-way ferrule 30 is provided to secure central portion 32 of suture material 26 as suture material 26 is drawn through bore 42 of one-way ferrule 30. This can be accomplished in a variety of known manners. In this embodiment, securing member 44 of one-way ferrule 30 is formed as a pair of inwardly projecting and proximally extending fingers 106 and 108 which are configured to frictionally grasp central portion 32 of suture material 26 as suture material 26 is drawn proximally through one-way ferrule 30.

Figure 7:
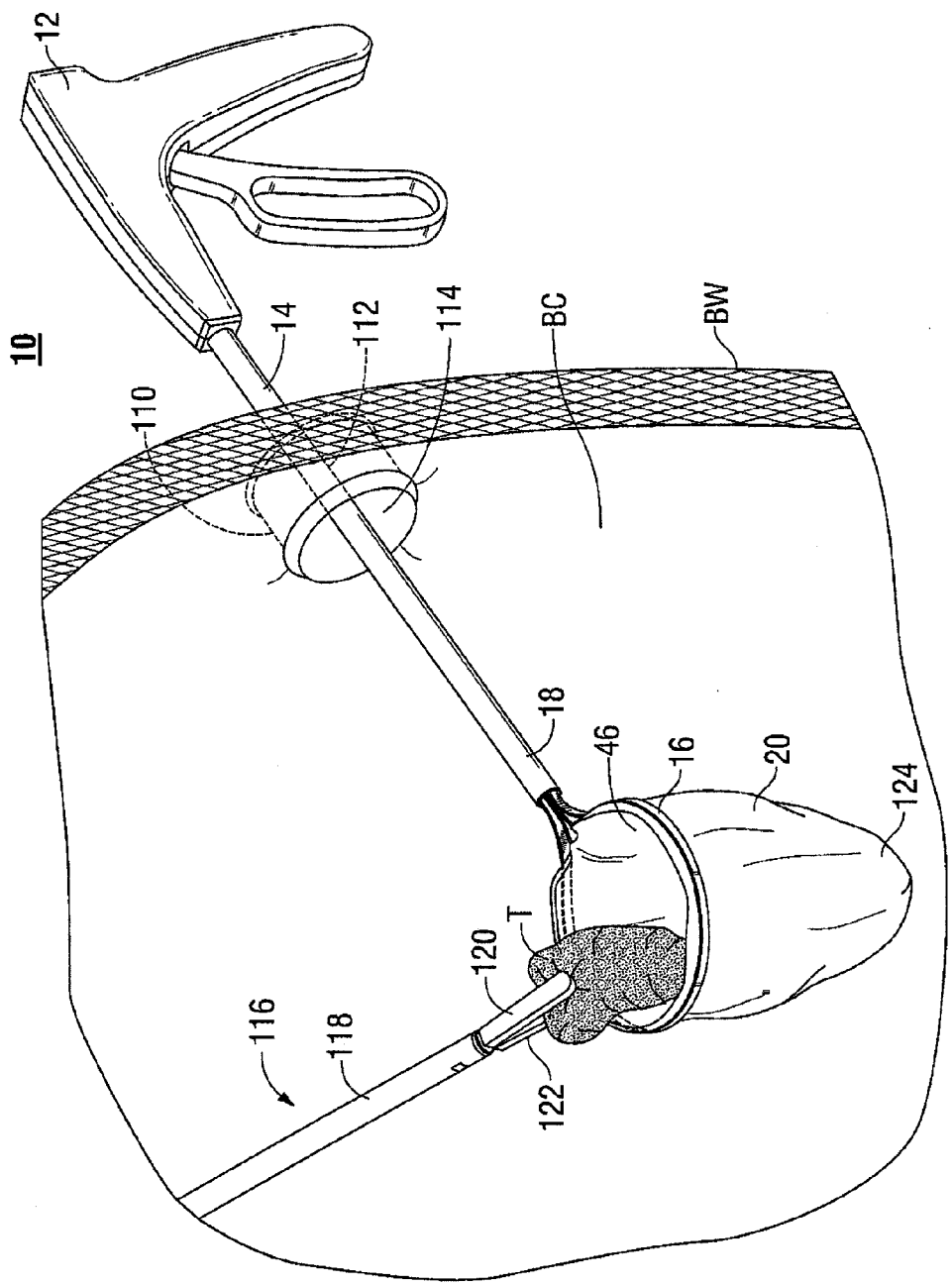
FIG. 7 is a perspective view of the specimen retrieval device inserted through a port through a body wall and a specimen being deposited in a specimen removal (retrieval) bag of the specimen retrieval device.

Referring now to FIGS. 7-14, and initially with regard to FIG. 7, the use of specimen retrieval device 10 to collect and retrieve a body organ or tissue sample T from within a body cavity BC of a patient will now be described. Initially, a surgical access port 110 is inserted through a body wall BW of the patient to provide access to body cavity BC. Surgical access port 110 includes a throughbore 112 and a seal 114 for sealing about surgical instrumentation and preventing the escape of fluids or insufflation gases (if used in laparoscopic procedures). Thereafter, specimen retrieval device 10 is manipulated such that distal end 18 of elongate tubular member 14 along with flexible support band 16 and collection bag 20 pass through throughbore 112 and seal 114 of surgical access port 110 and are positioned adjacent tissue T in body cavity BC. During a surgical procedure, tissue T would have been excised or separated from surrounding tissues and a separate surgical instrument such as, for example, grasper 116 utilized to manipulate tissue T into collection bag 20. Specifically, a distal end 118 of grasper 116 is positioned adjacent tissue T such that first and second movable jaws 120 and 122 grasp tissue T and deposit tissue T through open upper end 46 of collection bag 20. It should be noted that while collection bag 20 has an open upper end 46 it is additionally includes a closed lower end 124 to retain tissue T.

Figure 8:
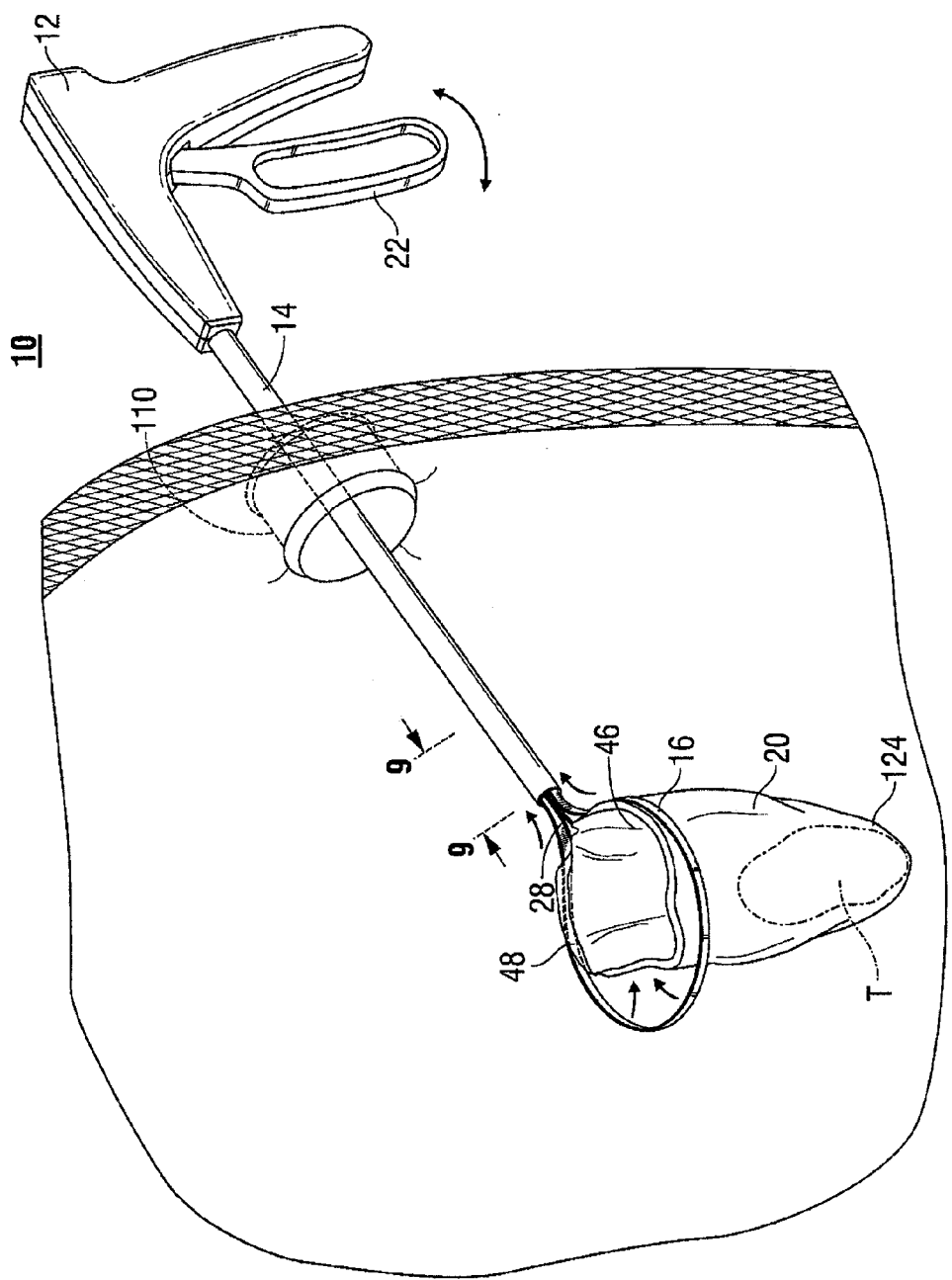
FIG. 8 is a perspective view similar to FIG. 7 with the handle of the specimen retrieval device actuated to contract the suture loop about the specimen removal bag.
Figure 9:
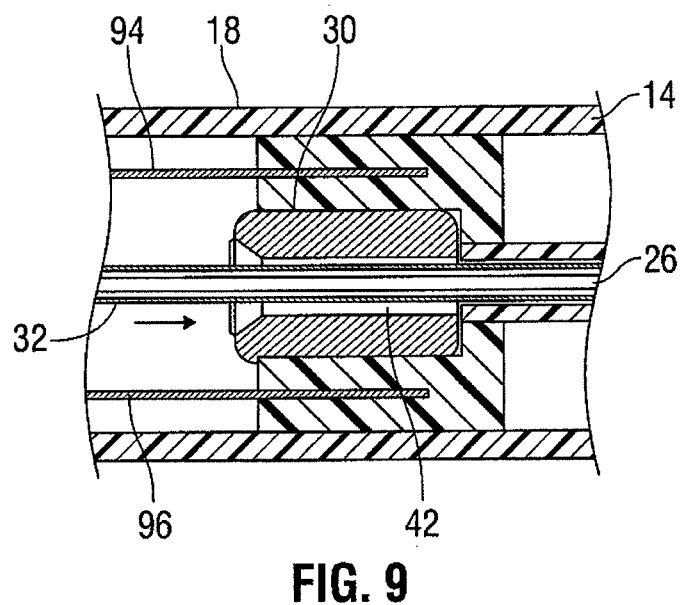
FIG. 9 is a cross-sectional view taken along line 9-9 of FIG. 8.

Referring now to FIG. 8, thereafter, trigger 22 is manipulated to draw distal loop portion 28 of suture material 26 through folded section 48 in open upper end 46 of collection bag 20 to detach open upper end 46 from flexible support band 16 and initiate closure of open upper end 46 of collection bag 20. As best shown in FIG. 9, central portion 32 of suture material 26 is drawn throughbore 42 (and thus securing member 44) in one-way ferrule 30.

Figure 10:
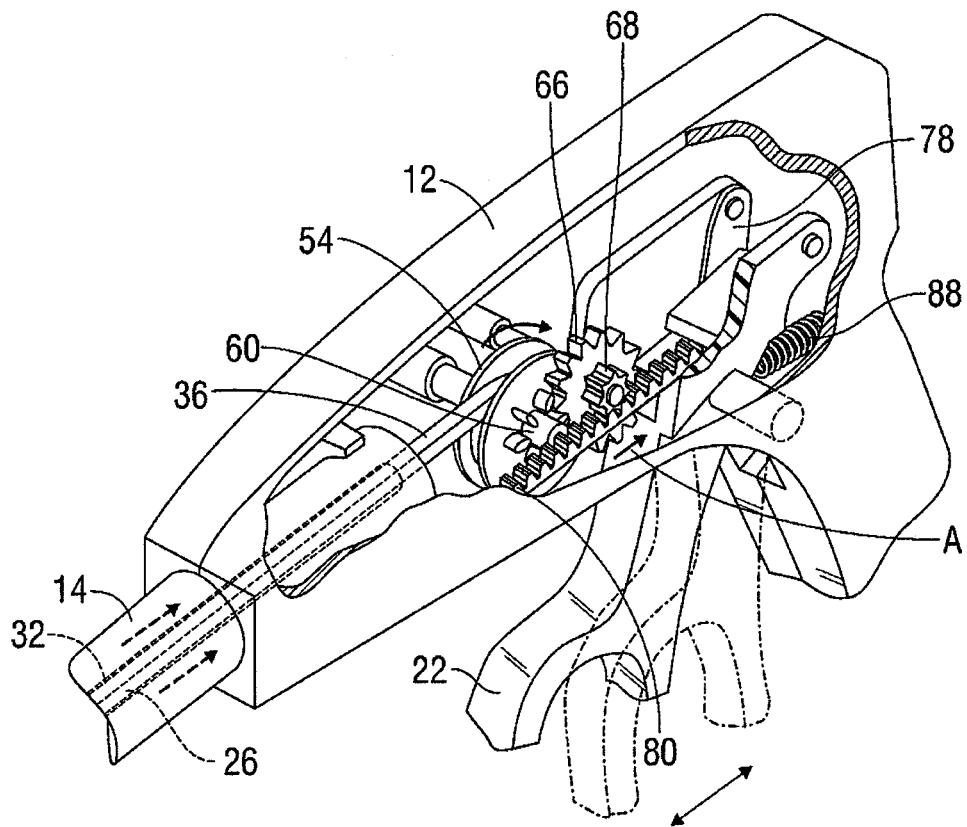
FIG. 10 is a perspective view, partially shown in section, of the handle portion of the specimen retrieval device of FIG. 1 during actuation.

With reference to FIG. 10, as trigger 22 is manipulated relative to handle portion 12, linkages 78 draw drive rack 80 proximally in the direction of arrow A to rotate drive gear 68 and therefore transmission gear 66 in a counterclockwise direction. As transmission gear 66 rotates in a counterclockwise direction, it rotates take-up gear 60 and thus take-up spool 54 in the clockwise direction thereby drawing proximal end 36 of central portion 32 of suture material 26 proximally into handle portion 12.

Figure 11:
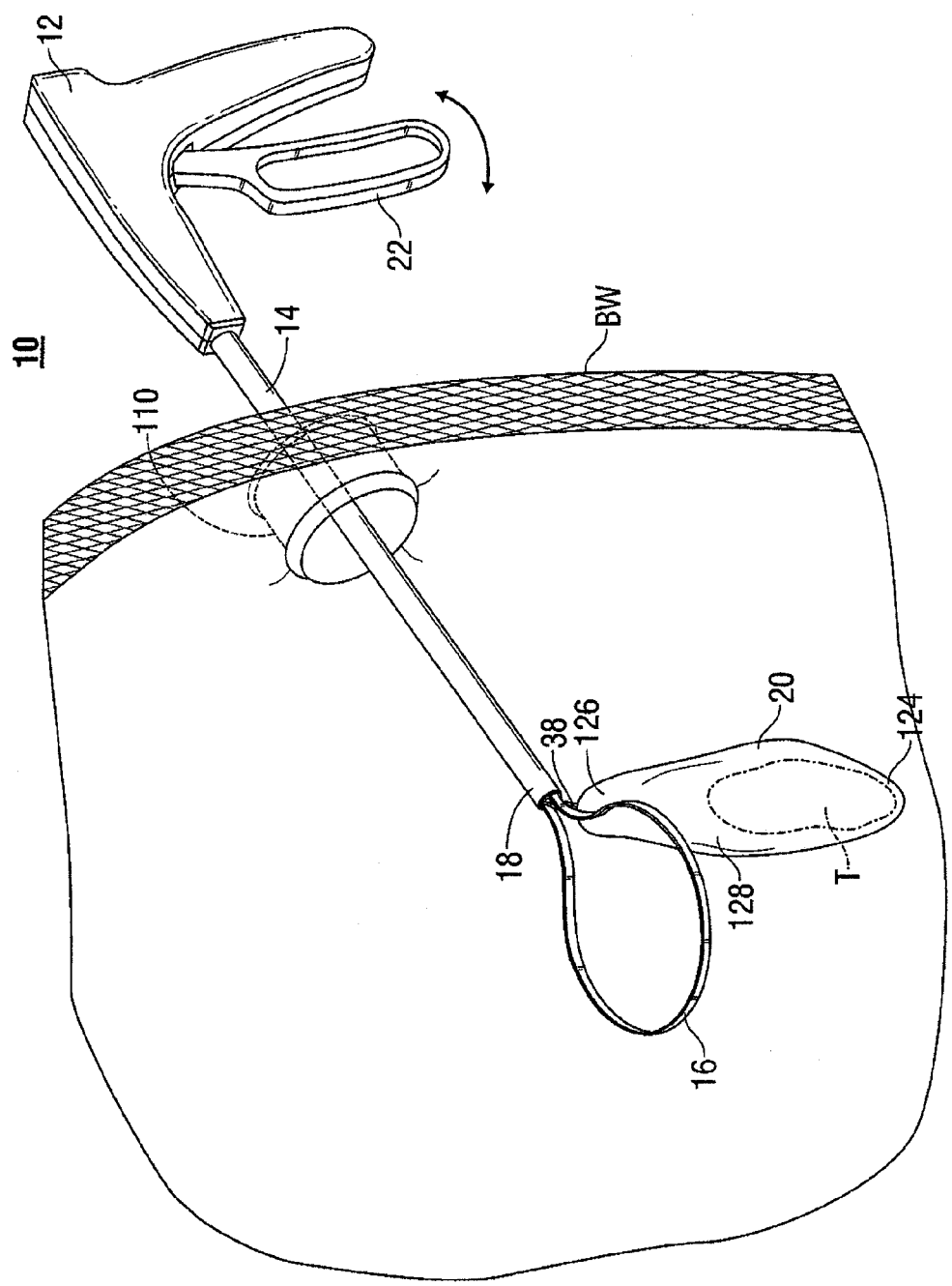
FIG. 11 is a perspective view of the specimen retrieval device similar to FIG. 7 with the suture loop fully contracted about the specimen removal bag.
Figure 12:
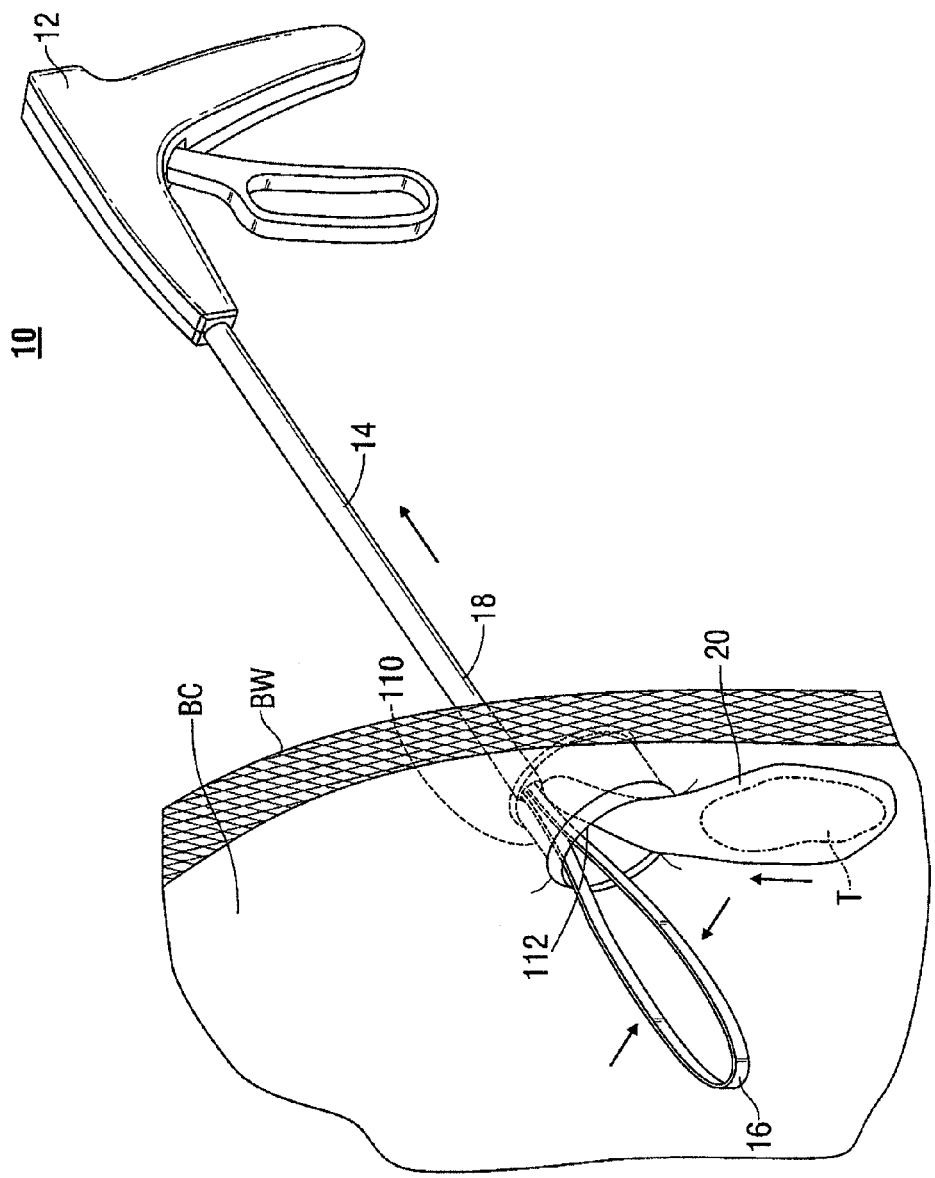
FIG. 12 is a perspective view of the specimen retrieval device similar to FIG. 7 showing the specimen removal bag and specimen being withdrawn through the port.

Referring now to FIG. 11, after complete actuation of trigger 22, distal end 38 of suture material 26 has fully closed distal loop portion 28 of suture material 26 about open upper end 46 of collection bag 20 to form a closed upper and 126 of collection bag 20 thereby securing tissue section T within an interior 128 of collection bag 20. Thereafter, with reference to FIG. 12, elongate tubular member 14 of specimen retrieval device 10 may be withdrawn through seal 114 in access port 110 thereby drawing collection bag 20, containing tissue T, and flexible support band 16 out of body cavity BC to complete the surgical procedure. In this manner, specimen retrieval device 10 including suture loop assembly 24 provides a simple and secure method of capturing a tissue section T within collection bag 24 later testing and analysis.

Figure 13:
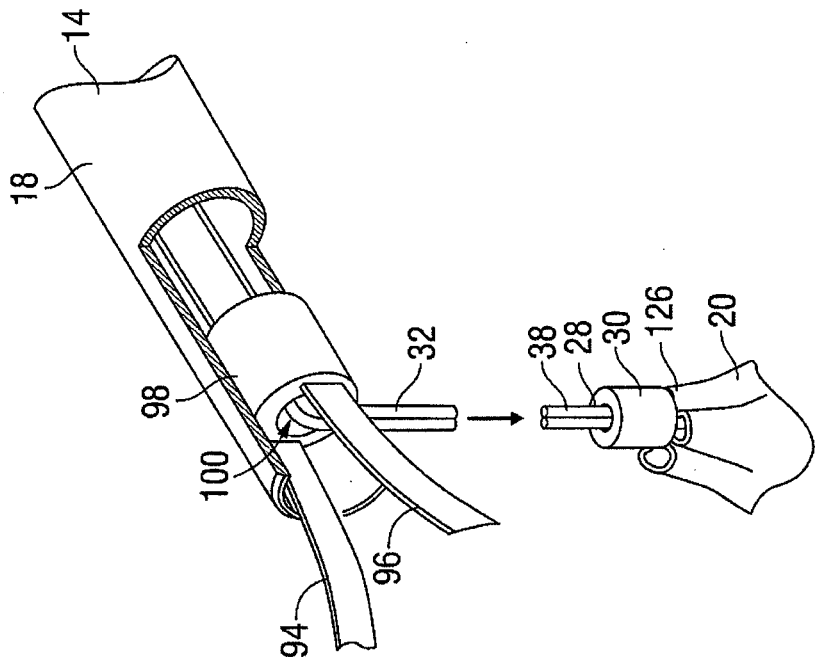
FIG. 13 is a perspective view, partially shown in section, of a distal end portion of the specimen retrieval device illustrating a first method of detaching the specimen removal bag and specimen from the specimen retrieval device.

Referring to FIG. 13, in an alternative method, collection bag 20 may be disconnected from distal end 18 of elongate tubular member 14 by cutting distal end 38 of suture material 26 and retrieving collection bag 20 separately from within a body cavity BC.

Figure 14:
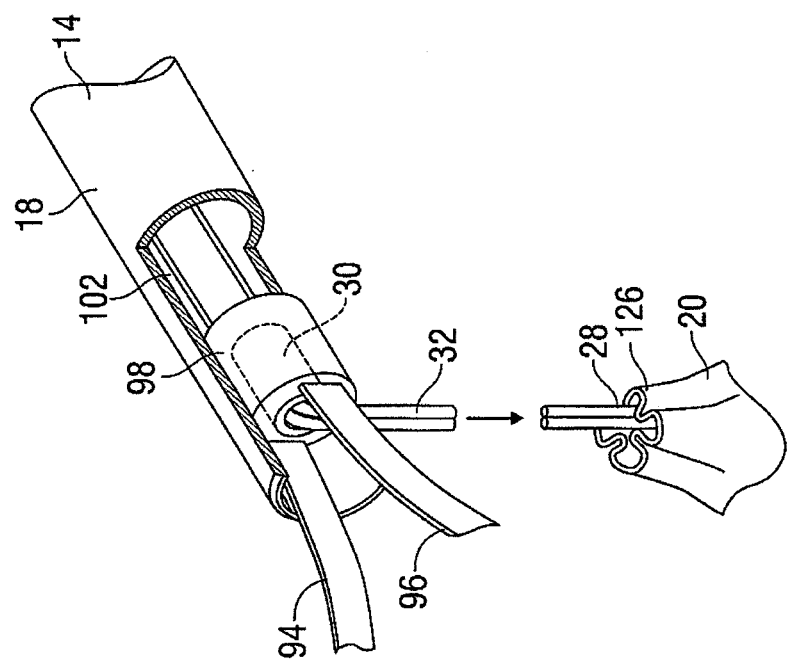
FIG. 14 is a perspective view, partially shown in section, of a distal end portion of the specimen retrieval device illustrating a second method of detaching the specimen removal bag and specimen from the specimen retrieval device.

With reference to FIG. 14, in a further alternative method, and as noted herein above, one-way ferrule 30 may be releasably supported within support collar 98 such that one-way ferrule 30 remains with collection bag 20 to maintain closed upper end 126 of collection bag 20 in a closed condition during removal. In this method, distal end 38 of suture material 26 is cut proximally of one-way ferrule 30 allowing one-way ferrule 30 and collection bag 20 to be removed from body cavity BC independently of the remainder of specimen retrieval device 10.

It will be understood that various modifications may be made to the embodiments disclosed herein. For example, flexible support band 16 may be configured to retract proximally within the elongate tubular member 14. Additionally, collection bag 20 may include reinforcing structures or other shapes to conform to various types of captured tissues. Therefore, the above description should not be construed as limiting, but merely as exemplifications of particular embodiments. Those skilled in the art will envision other modifications within the scope and spirit of the claims appended hereto.

What is claimed is:

1. A specimen retrieval device comprising:
a handle portion having a take-up spool;
a suture loop assembly, the suture loop assembly including a length of suture material having a double strand central portion and a single-strand distal loop portion extending distally from the central portion, and a one-way ferrule defining a ferrule bore, the double strand central portion passing into a first end of the ferrule bore of the one-way ferrule and from a second end of the ferrule bore, the one-way ferrule including a securing member to prevent the double strand central portion from moving through the ferrule bore in a first direction; and
a specimen retrieval bag, the suture material engageable with the specimen retrieval bag and operable to close the specimen retrieval bag, wherein the take-up spool is engageable with the proximal end of the length of suture.

2. The specimen retrieval device as recited in claim 1, wherein the length of suture material includes a pull loop extending proximally from the double strand central portion.

3. The specimen retrieval device as recited in claim 1, further comprising an elongate tubular member defining a tubular member bore and having a distal portion, wherein the one-way ferrule is positioned within the distal portion and the double strand central portion extends through the tubular member bore.

4. The specimen retrieval device as recited in claim 1, wherein the length of suture material is a single continuous length of suture material.

5. The specimen retrieval device as recited in claim 4, wherein the single continuous length of suture material is formed by molding a source material.

6. The specimen retrieval device as recited in claim 4, wherein the single continuous length of suture material is formed by securing free ends of a source material together.

7. The specimen retrieval device as recited in claim 4, wherein the single continuous length of suture material is formed of a synthetic material.

8. The specimen retrieval device as recited in claim 4, wherein the single continuous length of suture material is formed of a natural material.

9. A specimen retrieval device comprising:
a handle portion having a take-up spool;
an elongate tubular member extending distally from the handle portion;
a collection bag extending from a distal end of the elongate tubular member; and
a suture loop assembly engageable with the collection bag and extending proximally through the elongate tubular member, the suture loop assembly including a length of suture having a distal loop engageable with the collection bag, a central portion, a proximal end, and a one-way ferrule positioned within the elongate tubular member about the central portion, the one-way ferrule including a securing member to prevent the central portion of the length of suture from moving through the one-way ferrule in a first direction, wherein the take-up spool is engageable with the proximal end of the length of suture.

10. The specimen retrieval device as recited in claim 9, further comprising a trigger engageable with the take-up spool to rotate the take-up spool and close the collection bag.

11. The specimen retrieval device as recited in claim 10, wherein the handle portion includes a longitudinally movable rack engageable with the trigger and the take-up spool.

12. The specimen retrieval device as recited in claim 11, wherein the handle portion further includes a take-up gear provided on the take-up spool.

13. The specimen retrieval device as recited in claim 12, wherein the handle portion further includes a transmission gear engageable with the take-up gear, wherein the transmission gear includes a drive gear engageable with the longitudinally movable rack.

14. The specimen retrieval device as recited in claim 10, further comprising a return spring engageable with the trigger and the handle portion to maintain the trigger in a pre-fired condition.

15. The specimen retrieval device as recited in claim 9, wherein the one-way ferrule defines a ferrule bore and the length of suture extends into a first end of the ferrule bore and from a second end of the ferrule bore.

* * * * *